United States Patent [19]

McFarland et al.

[11] Patent Number: 4,655,757
[45] Date of Patent: Apr. 7, 1987

[54] SELECTIVE LAYERING OF SUPERABSORBENTS IN MELTBLOWN SUBSTRATES

[75] Inventors: Timothy M. McFarland, Neenah; Theodore B. Lang, Menasha, both of Wis.

[73] Assignee: Kimberly-Clark Corporation, Neenah, Wis.

[21] Appl. No.: 835,009

[22] Filed: Feb. 28, 1986

Related U.S. Application Data

[62] Division of Ser. No. 602,993, Apr. 23, 1984, Pat. No. 4,604,313.

[51] Int. Cl.⁴ ............................................. A61F 13/16
[52] U.S. Cl. ................................. 604/366; 604/367; 604/368; 604/378
[58] Field of Search ............... 604/366, 368, 370, 371, 604/372, 378, 367

[56] References Cited

U.S. PATENT DOCUMENTS

| | | | |
|---|---|---|---|
| 4,100,324 | 7/1978 | Anderson et al. | 428/288 |
| 4,297,410 | 10/1981 | Tsuchiya et al. | 428/283 |
| 4,333,464 | 6/1982 | Nakamo | 428/407 |
| 4,338,371 | 7/1982 | Dawn et al. | 428/283 |
| 4,340,556 | 7/1982 | Ciencewicki | 264/109 |
| 4,372,312 | 2/1983 | Fendler et al. | 604/370 |
| 4,429,001 | 1/1984 | Koplin et al. | 428/283 |
| 4,537,590 | 8/1985 | Pieniak et al. | 428/283 |

FOREIGN PATENT DOCUMENTS

| | | | |
|---|---|---|---|
| 960427 | 6/1964 | United Kingdom | 604/366 |
| 2113731 | 8/1983 | United Kingdom | |

Primary Examiner—James J. Bell
Attorney, Agent, or Firm—P. A. Leipold; D. L. Traut; J. J. Duggan

[57] ABSTRACT

The invention generally provides for formation of meltblown material containing wood fiber on to a continuous foraminous belt. During formation a polymer and wood fiber first layer is applied to a moving belt from at least one bank of meltblown forming apparatus. This first layer does not contain superabsorbent. The belt carrying the first layer passes beneath at least one further source of meltblown fiber into which superabsorbent is added along with the wood fibers. This provides at least one additional layer integrally connected to the first-formed layer and having superabsorbent properties. The first layer acts to aid in trapping of any superabsorbent which is not immediately entangled in the meltblown and wood fibers and prevents it passing through the forming belt.

4 Claims, 8 Drawing Figures

SELECTIVE LAYERING OF SUPERABSORBENTS IN MELTBLOWN SUBSTRATES

This application is a divisional of U.S. Ser. No. 602,993 filed Apr. 23, 1984, now U.S. Pat. No. 4,604,313.

TECHNICAL FIELD

This invention relates to nonwoven fabrics and in particular those comprising a matrix of meltblown polymer fibers and more particularly to a wood pulp containing nonwoven fabric which additionally contains a particulate superabsorbent material.

BACKGROUND ART

It is known to form blown fibers of polyolefin such as polyethylene or polypropylene. Such meltblown fibers are known for use in wipes and other disposable items.

It is also been known as disclosed in U.S. Pat. No. 4,100,324 Anderson et al. to form nonwoven fabric materials of long thermoplastic polymer microfibers that have entangled therein wood pulp fibers. Such materials have found use in wipes and as absorbent materials for feminine care and incontinent products.

It has been suggested in the British Patent Application Publication No. 2,113,731 of Aug. 10, 1983, that the meltblown fiber having wood pulp fibers may be further supplied during forming with another absorbent material such as a superabsorbent or clay material. It is disclosed in the above United Kingdom Patent Application Publication that powdered superabsorbent may be added to the meltblown material during formation and that the majority of the particles will be entrapped into the material as it is gathered on a forming surface. The addition of superabsorbent particles to meltblown materials have also been suggested in U.S. Pat. No. 4,429,001—Koplin et al.

The use of superabsorbents in combination with fibrous material in an absorbent garment has been suggested by U.S. Pat. No. 4,338,371 Dawn et al. in which a layer of superabsorbent material containing superabsorbent is provided in a garment for utilization by astronauts for extravehicular activity. U.S. Pat. No. 4,297,410 Tsuchiya et al. also discloses a structure wherein a superabsorbent layer is placed between nonwoven fabric layers.

There have been several difficulties in prior materials utilizing superabsorbents. One difficulty has been that the superabsorbent materials exhibit a phenomenon usually referred to as gel-blocking. When this occurs the superabsorbents that are first exposed to liquids swell and block access of the liquid to the remaining superabsorbent. A preferred present practice attempts to overcome the gel-blocking phenomenon by sandwiching either particulate or film forms of superabsorbent between tissue or similar materials. This technique, however, tends to restrict the uptake of fluids by the superabsorbents, and adds cost to the superabsorbent material. Another difficulty with many superabsorbent containing materials is that the hydrogel superabsorbents when wet have an uncomfortable, clammy, slimy feel to them. The use of these materials in applications in which they are exposed to the body has been particularly difficult due to the slimy, unpleasant feel. There also has been difficulty in the processes in which air-forming is used in combination with particulate superabsorbents. Air-forming processes require the removal of air from beneath the forming surface. During air removal the particulate superabsorbents tend to also be removed as they are primarily held by physical entanglement and are not chemically bound with the meltblown thermoplastic fibers. The difficulties caused by sliminess have been attempted to be overcome by effectively burying the superabsorbent containing ply(s) beneath one or more plies that do not contain superabsorbent material.

Therefore, there is a need for an improved combination of superabsorbent material and fibrous material in which gel-blocking is minimal and superabsorbent is not wasted (by passing through the forming process, and being caught by the dust collector), and costly plying to mask the clammy, slimy feel of superabsorbent materials is unnecessary. There is also a need for a nonwoven fibrous material that acts as a matrix in which the particulate superabsorbents may be easily accessible to fluids and may be free to expand.

DISCLOSURE OF THE INVENTION

An object of this invention is to form a superabsorbent containing nonwoven fibrous material that does not present a slimy surface when wet.

An additional object of this invention to form a nonwoven fibrous material without a substantial loss of superabsorbent particulate during formation.

A further object of this invention is to form an absorbent nonwoven fibrous material that presents a drier feeling surface after fluid absorption.

These and other objects of the invention are generally accomplished by providing for formation of meltblown polymer material containing wood or other staple fiber and superabsorbent on a continuous forming wire or other foraminous belt. During formation a first layer of polymer fibers and entangled wood or other staple fibers is applied to the moving wire from at least one bank of meltblown fiber forming apparatus. This first layer does not contain superabsorbent. The wire carrying the first layer passes beneath at least one further source of meltblown fiber into which superabsorbent is added along with the wood or other staple fibers. This provides at least one additional layer integrally connected to the first-formed layer and having superabsorbent properties. The first layer acts to aid in trapping of any superabsorbent which is not immediately entangled in the meltblown and wood fibers and prevents its passing through the forming belt. The first layer also is the preferred body side in use as it will not be slimy and will feel drier than the superabsorbent containing side.

In a preferred form a single layer of air-formed meltblown fiber containing wood fibers is placed onto a moving forming wire and then passed beneath a second air stream containing a combination of meltblown polymer fibers, wood fibers and superabsorbent. The second bank forms a superabsorbent-containing layer that will be integrally connected to the first-formed layer, thereby forming a composite material that has its layers integrally connected and presents a cloth-like surface on one side and a superabsorbent-containing surface on the other. Therefore, this allows the placement of the cloth-like surface towards the skin of the wearer while the superabsorbent-containing surface is on the interior of the material during use as a dressing or incontinent product.

MODES FOR CARRYING OUT THE INVENTION

The ivention has numerous advantages over prior products and methods for combination of superabsorbents with other carrier and absorbent materials. In the invention the superabsorbent is carried in an integral structure in such a way that the superabsorbent will not contact the skin when the structure is utilized in a dressing, diaper, or incontinent product. The prevention of skin contact has the advantage that the slimy and clammy feel of wet superabsorbent is not felt, and further, the superabsorbent will not cause irritation to the skin of the wearer. Another advantage is that the particulate superabsorbent is generally encassed within the dressing, garment or other absorbent product such that any particles that become loose are retained in the product rather than leaving the surface. If the absorbent particles leave the surface they, of course, are not available for absorbency, and further cause the product to be considered undesirable as the powder is annoying to the wearer or person manipulating the absorbent device.

Another advantage of the system of the invention is that during the forming process the superabsorbent is not removed by the air-removal system in an excessive amount. If applied in the first layer of meltblown and wood or staple fibers directly at the forming wire, a significant quantity of powdered superabsorbent will pass through and be removed by the air-forming system. This particulate is generally wasted as it is not recoverable efficiently. These and other advantages of the invention will be apparent from the detailed description provided below.

Figure 1:
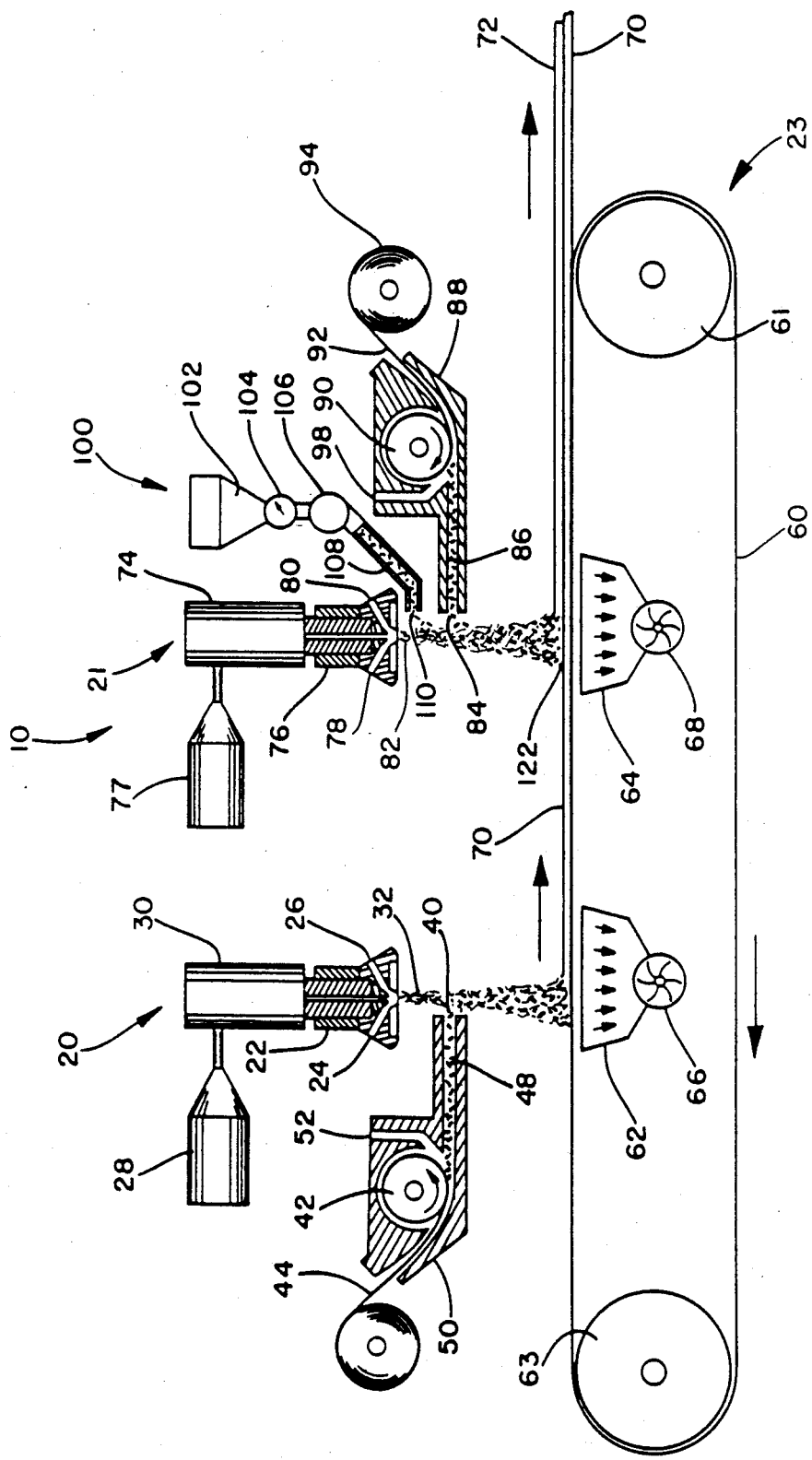
FIG. 1 illustrates a device of the invention having two banks for formation of meltblown fibers with the downstream bank additionally having provision for application of superabsorbent material.

FIG. 1 illustrates the forming apparatus generally indicated as 10 which is composed of two meltblown units 20 and 21, and a movable foraminous belt apparatus 23. The foraminous belt is preferably a wire belt. The meltblown apparatus 20 is composed of a die head 22 through which air streams 24 and 26 pass. Supply and delivery device 28 delivers polymer to extruder 30 for delivery to the die head 22. The polymer leaves extruder head 22 and is combined with primary air stream 32, where the fine polymer streams leaving the die head 22 are attenuated by the converging flows of high velocity heated gas (usually air) supplied through nozzles 24 and 26 to break the polymer streams into discontinuous microfibers of small diameter. The die head preferably includes at least one straight row of extrusion apertures. In general, the resulting microfibers have an average fiber diameter of up to only about 10 microns with very few, if any, of the microfibers exceeding 10 microns in diameter. In general, the average diameter of the microfibers is usually greater than about 1 micron and within the range of about 2 to about 6 microns, often averaging about 5 microns. While the microfibers are predominantly discontinuous, they generally have a length exceeding that normally associated with staple fibers.

The primary gas stream 32 is merged with a secondary gas stream containing individualized wood pulp or other staple fibers so as to integrate the two different fibrous materials in a single step. The individualized wood pulp fibers typically have a length of about 0.5 to 10 millimeters and a length to maximum width ratio of about 10 to 1 to 400 to 1. A typical cross-section has a irregular width of 10 microns and a thickness of 5 microns. In the illustrated arrangement a secondary gas stream 40 is formed by a pulp sheet divellicating apparatus of the type described in U.S. Pat. No. 3,793,678 to Appel. This apparatus comprises a conventional picker roll 42 having picking teeth for divellicating pulp sheets 44 into individual fibers. The pulp sheets 44 are fed radially along a picker roll radius to the picker roll 42. It is the teeth of the picker roll 42 that allocate the pulp sheets 44 into individual fibers, the resulting separated fibers are conveyed toward the primary air stream 32 through a nozzle or duct 48. A housing 50 covers the picker roll 42. A passageway 52 provides process air to the picker roll in sufficient quantity to provide a medium for conveying the fibers through the forming duct 48 at a velocity approaching that of the picker teeth. The air may be supplied by conventional means, i.e., a blower not shown. It has been found that in order to avoid fiber flocking, the individual fibers should be conveyed through the duct 48 at substantially the same velocity at which they leave the picker teeth after separation from the pulp sheets 44. The apparatus described for formation of the article of microfibers having wood fibers entangled therein now referred to as coform is known and is more fully described in U.S. Pat. No. 4,100,324 Anderson et al. which is incorporated herein by reference. Air stream 32 having wood fibers from stream 48 incorporated therein then is placed onto a moving belt 60 that passes beneath the forming die 22 as the microfibers and air stream are directed downwardly. The foraminous belt 60 is provided with suction boxes 62 and 64 driven by blowers 66 and 68 that withdraw air from beneath the foraminous belt 60 and provide for uniform laydown of the fibers onto the belt. Belt 60 in addition to being supported by roll 61 is also supported by roll 63. While illustrated with two suction devices, the number and size of the suction devices below the belt may be varied. Further, the forming device is provided with dust collector devices, not shown, to prevent escape of superabsorbent and fibers to the atmosphere.

As illustrated in FIG. 1, a meltblowing device 20 lays down a layer of meltblown polymer fibers having wood or other staple fibers entangled therein as layer 70. This passes beneath the second meltblowing device 21 where a second layer 72 is placed thereon and joined to the layer 70. Layer 72 is formed by device 21 that is composed of an extruder 74 fed by material supply device 77. Extruder 74 feeds to die head 76 that is generally similar to die head 22, having high velocity air nozzles for supplying air to extrusion stream 82. As the air streams from nozzle 78 and 80 merge into stream 82 and entrain the extruded fibers, they are meltblown into microfibers and mixed with a stream of wood fibers 84, exiting through nozzle 86 from the picker device 88. In picker device 88 the picker roll 90 rotates and divellicates pulp sheets 92 as they are unrolled from supply roll 94. The pulp sheets are divellicated and passed through nozzle 86 to join the meltblown stream 82. Process air is supplied through duct 98 of the picker roll housing 88. The meltblown extrusion device 21 differs from that of 20 in that there additionally is provided a source of superabsorbent material generally indicated as apparatus 100 composed of storage hopper 102, having a feed device 104 leading to a source of high velocity air 106, and a nozzle or duct 108 providing a stream of superabsorbent 110 to the meltblown stream 82 at a point slightly above the point where nozzle 86 provides a stream of cellulose fibers 84. The superabsorbent is entrained in air stream 82 and becomes co-mingled and entangled with the meltblown fibers and the cellulose fibers. It then is laid onto the layer 70 at 122 as layer 72. Suction box 64 aids in laydown. The fibers of the second layer when laid down become somewhat entangled with fibers on the surface of first fiber layer 70. This entanglement is such that an integral unit is formed, although if the layers 70 and 72 are pulled apart they will generally separate on the formation line. However, the entanglement is such that an integral structure for processing and use purposes is formed. The composite structure of layer 72 and 70 after leaving the support roller 61 may be further processed by known means such as cutters and stackers, not shown. Belt 60 in addition to being supported by roll 61 is also supported by roll 63.

Figure 2:
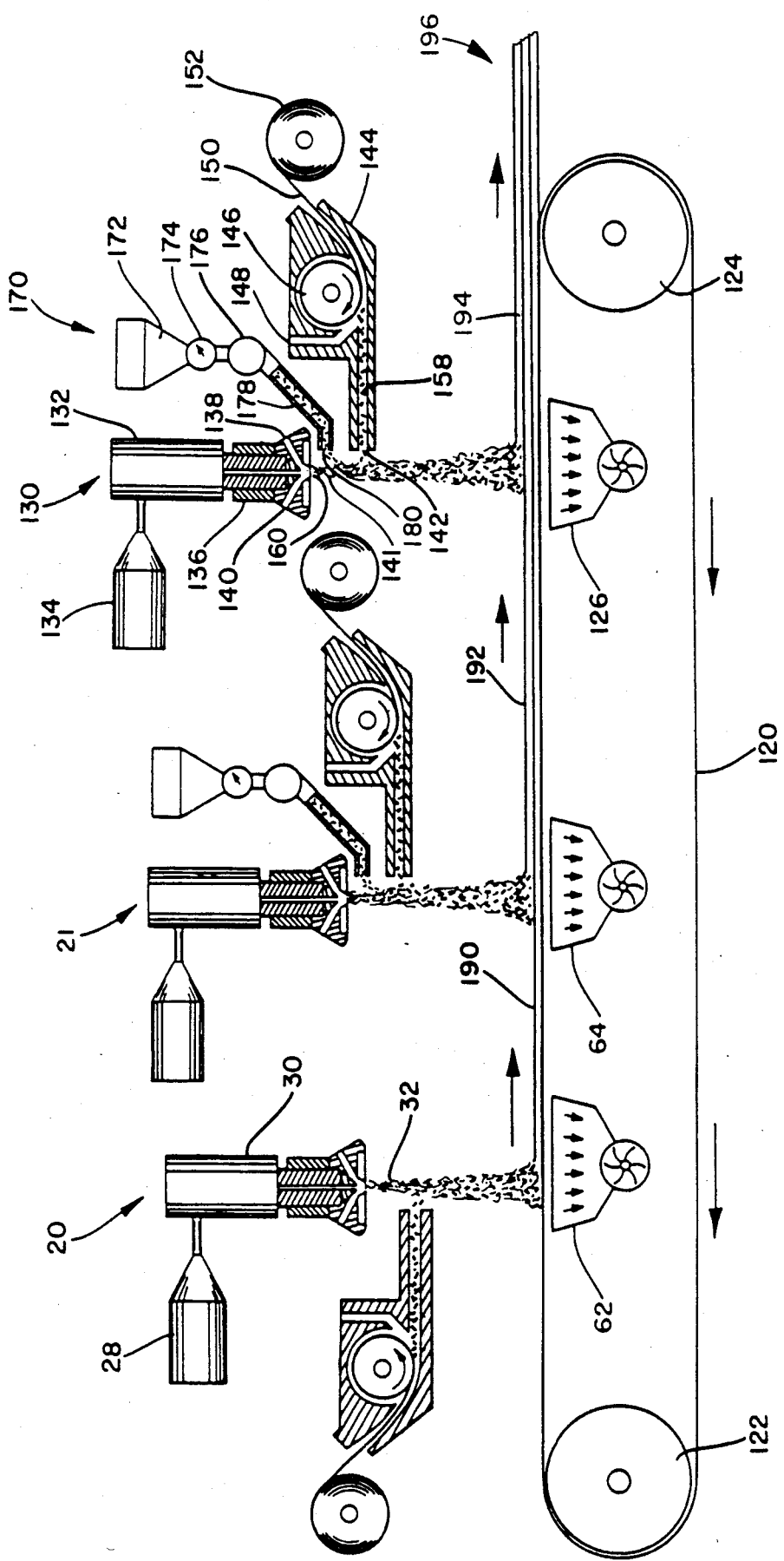
FIG. 2 has illustrates of a belt-forming unit for meltblown materials in which three banks for formation of meltblown material are shown.

The apparatus of FIG. 2 is a modified form of the apparatus of FIG. 1 in which meltblowing devices 20 and 21, as previously described, are placed above a foraminous belt 120 that is driven by rolls 122 and 124. Below the belt are located at least 3 suction devices 62, 64, and 126. In addition to meltblown devices 20 and 21, previously described, there is now a third meltblown apparatus, device 130. This third device also comprises, as systems 20 and 21 do, an extruder 132 fed by supply device 134, leading to extrusion head 136. The extrusion head 136 has therein two channels 138 and 140 that are provided with a source of subsonic air not shown to provide a primary air stream 160 into which polymer is extruded by extrusion head 136. The primary air stream 160 having entrained therein the meltblown fibers has added to it fiber cellulose from picker device 144. The picker device 144 is comprised of a picker roll 146 that has a air channel 148 as a source of primary air to the picker roll. The picker roll 146 divellicates pulp 150 that is supplied from pulp roll 152. The divellicated fibers pass through nozzle or channel 158 and are blown into the meltblown stream 141 as a stream of fibers 142. Apparatus 130 also has a feed device 170 that is composed of a storage device 172 for superabsorbent material. The storage device 172 has a feeder 174 attached thereto that feeds into a source of subsonic air 176. The superabsorbent entrained in the subsonic air passes through feeder nozzle 178 and is applied to the polymer stream as a stream of superabsorbent entrained in a tertiary air stream 180. In FIG. 2 the first layer laid down by device 20 is indicated as 190. The second layer containing superabsorbent material is 192 and the third layer that is sourced from apparatus 130 is laid down as layer 194. These layers are integrally connected by entanglement of fibers at laydown. The three-layered sheet 196 after leaving the forming device may be treated by conventional means such as cutters and stackers to prepare it for use in an absorbent product. It may be seen that the invention as illustrated in FIG. 2 is capable of forming nonwoven webs with superabsorbent in either or both of two upper layers or with only a center section containing superabsorbent if the superabsorbent feeder 170 is not operated.

Figure 3:
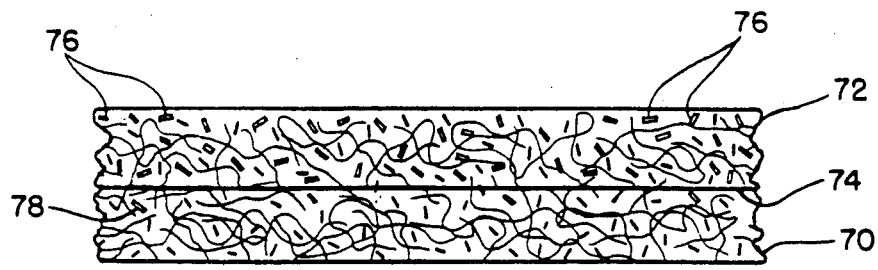
FIG. 3 illustrates a cross-section of a two-layer superabsorbent containing nonwoven of the invention.

FIG. 3 is illustrative of a cross-section through a integral two-layered sheet such as formed by the process and apparatus as illustrated by FIG. 1. Layer 70 is composed of a tangled structure of wood or other fiber and meltblown polymer fibers. Layer 72 is a tangled structure of meltblown fibers and wood fiber, in addition containing superabsorbent particles 76. The area of joinder of the two layers at 74 is somewhat irregular as the fibers from each layer are somewhat intermingled and it is noted that some particles of superabsorbent such as 78 have crossed into the lower layer drawn there by the vacuum effect of the suction below the foraminous belt during formation.

Figure 4:
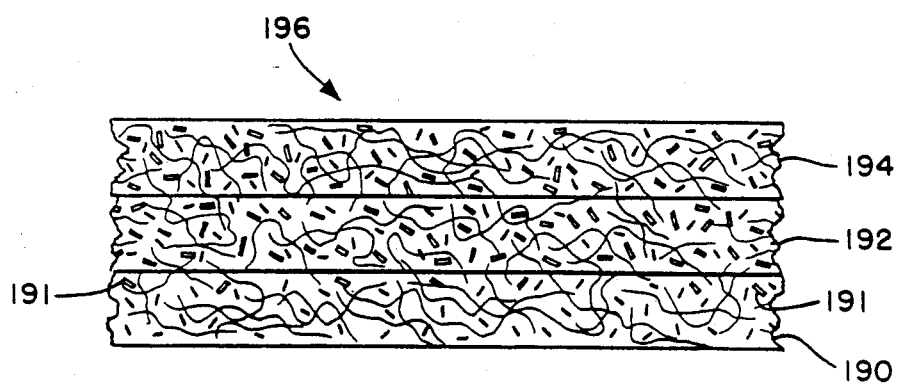
FIG. 4 is a cross-section of the material formed by the process and apparatus of FIG. 2.

FIG. 4 is illustrative of a three-layered structure such as may be formed by the process and apparatus of FIG. 2. As illustrated in the cross-section, the layer 190 is formed of entangled polymer and cellulose fibers with only stray particles of superabsorbent such as 191. Layers 192 and 194 are formed of tangled polymer fibers, cellulose fibers, and superabsorbent particles. The layers themselves have somewhat intermingled surfaces and form an integral structure.

Figure 6:
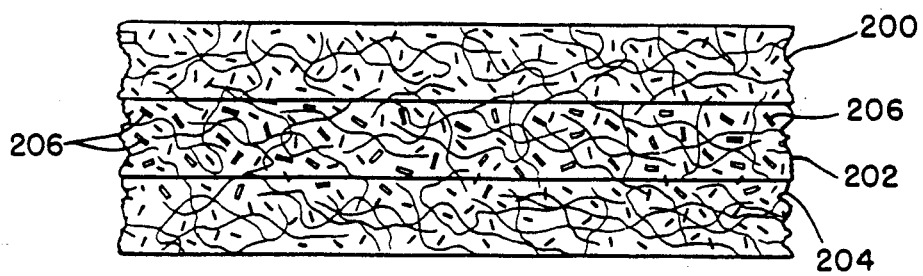
FIG. 6 illustrates a three-layered structure in accordance with the invention in which the middle layer contains superabsorbent.

FIG. 6 illustrates an alternate embodiment of a nonwoven structure in accordance with the invention. In FIG. 6 an integral body having three layers 200, 202, and 204 is illustrated. Layers 200 and 204 are formed of entangled polymer and cellulose fibers while these surface layers are integrally connected to a center layer 202 which is formed of intermingled and intertwined cellulose fibers, polymer fibers and superabsorbent particles 206. This structure has the advantage that the superabsorbent material is not exposed on either surface. Therefore, in use this structure will not present a slimy surface. Further, the shaking loose of superabsorbent particles is minimized as is the possibility of allergic reaction caused by the handling of the superabsorbent containing nonwoven material.

Figure 5:
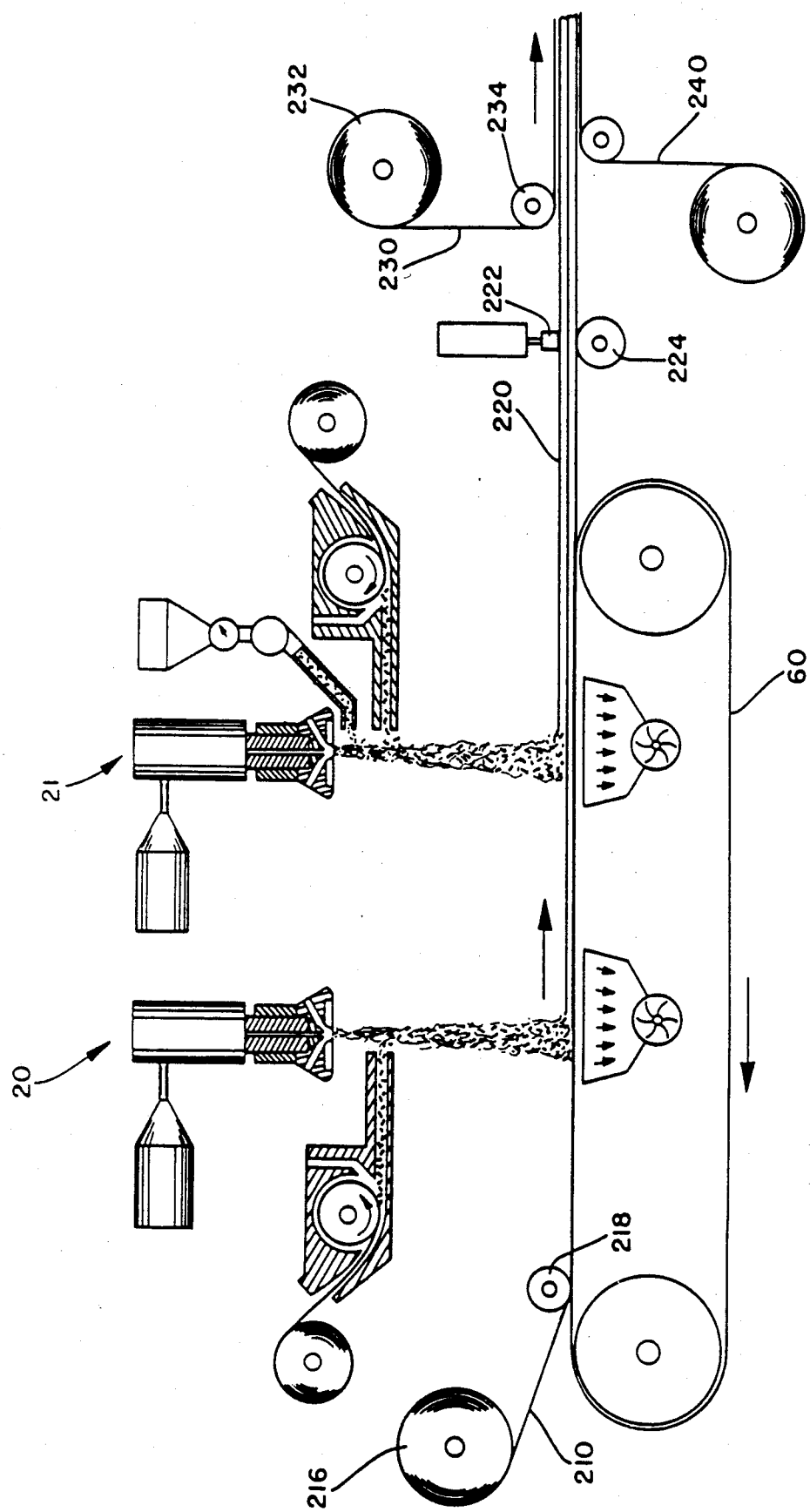
FIG. 5 illustrates an alternate embodiment of the invention in which the absorbent layer structure of the invention is provided with embossing and combined with a carrier sheet.

FIG. 5 illustrates apparatus such as previously illustrated in FIG. 1 but including various optional peripheral devices that may be included with a forming system in accordance with the invention. A base sheet 210 may be placed onto the foraminous belt 60 prior to application of the first meltblown fiber stream. The base sheet 210 ordinarily would be a pervious sheet such as a spunbonded fabric sheet that would not interfere with air flow through the belt 60. The pervious material would be applied from roll 216 passing under applicator roll 218 onto the belt 60. It may be desired that the strength of the composite web 220 be improved by embossing ultrasonically as by an ultrasonic embossing station comprising an ultrasonic calendering head 222 vibrating against a patterned anvil roll 224. The embossing conditions as well as the embossing pattern may be selected to provide the desired characteristics to the final product. In the preferred intermittent pattern it is preferred that the area of the web occupied by the embossed area, after passing through the embossing nip, be about 5 to about 50 percent of the surface area of the material, the particular embossing conditions for any given material will depend on the composition of the material. It is also known to carry on embossing by the use of heated patterned embossing rolls. The embossing process lowers the absorbency of the product although it does increase strength and improve appearance. It is further possible to apply a top sheet 230 to the composite sheet 220. The top sheet may be either a pervious sheet, an impervious layer, or another absorbent material. Top sheet 230 is applied from roll 232 under applicator roll 234. It also may be desirable to apply a carrier or bottom sheet 240 beneath the composite 220. This sheet may be particularly desirable if a forming sheet 210 is not used as it will aid in handling of the product and then may be discarded.

Figure 7:
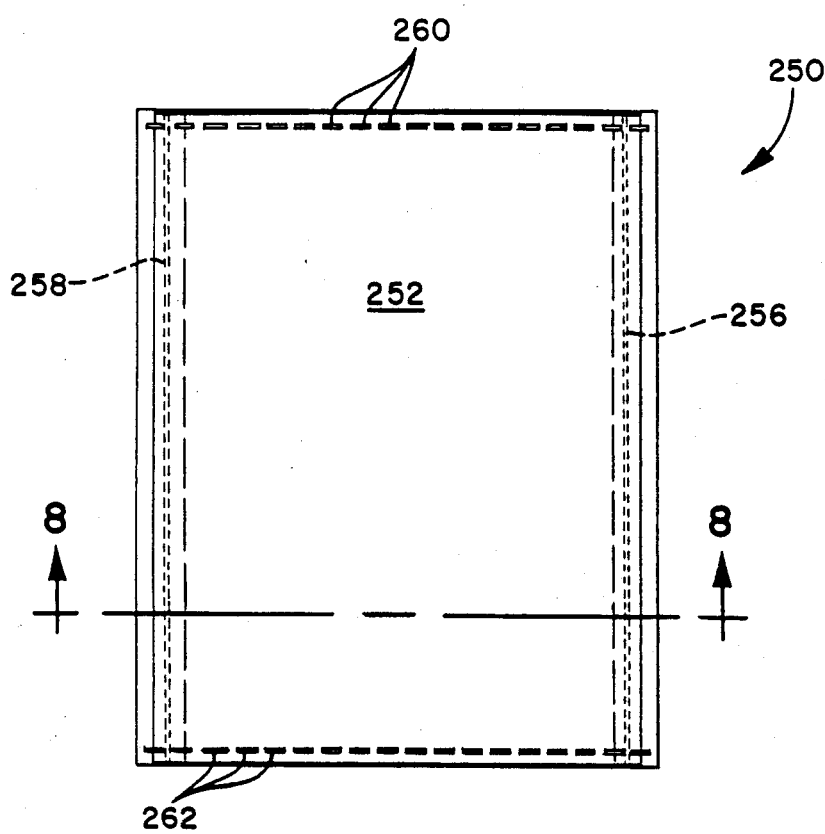
FIG. 7 is a view of a dressing formed from the absorbent material of the invention.
Figure 8:
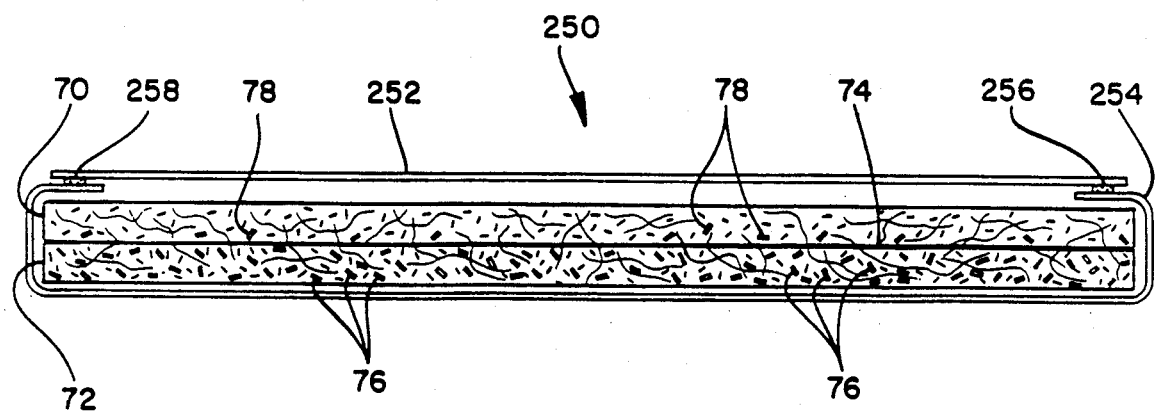
FIG. 8 is a cross-section of the dressing of FIG. 7 taken on line 18-8 of FIG. 7.

The dressing 250 of FIGS. 7 and 8 is formed with the absorbent material of FIG. 3. The dressing 250 has an impervious polymer wrapping 254 and a body-side pervious member 252. The impervious wrapping is adhered to the pervious liner by glue lines at 256 and 258. The ends of the dressing are ultrasonicly sealed at 260 and 262. The coform material of layer 70 that does not have superabsorbent is exposed to the body of the wearer. The dressing 250 may be utilized for absorption of any body exudate. Typical of such uses would be as catamenial devices, diapers, or wound dressings. A preferred use is in incontinent care devices as the absorbent is capable of holding large amounts of liquid such as are released in an incontinent adult.

The product produced by the process and apparatus of the invention has the advantage as set forth above that the slimy superabsorbent will not be presented to a bodily surface. It further has the advantage that when the composite of polymer fiber and cellulose fiber that overlays the superabsorbent layer is set, the wetness will spread on the exposed surface layer prior to being absorbed by the superabsorbent layer. This then presents a drier surface to the wearer after the superabsorbent layer has absorbed the liquid from the surface layer. The drier surface is also less likely to leak when compressed. The composite structure then presents a drier feel than the layer of composite of microfilaments of polymer and wood fiber as the wetness is absorbed by the superabsorbent integral layer with which it is in contact. The composition of the meltblown layer containing cellulose fibers and the layer containing meltblown, cellulose and superabsorbent may be varied over a wide range. The combination of air-formed meltblown polymer and cellulose fiber is commonly called coform. This material may vary between about 10 percent polymer and 90 percent polymer and between 90 percent cellulose and 10 percent cellulose. Generally, there is also a surfactant that is added to the product to aid in wetting of the polypropylene.

The superabsorbent material suitable for the invention may be any superabsorbent that will maintain its particle integrity during the meltblowing process and exhibit good storage, handling, and resistance to gel-blocking properties. Typical of such materials are the water-insoluble hydrocolloidal particles derived from starches that will swell but not dissolve when exposed to water. Suitable for the invention are those superabsorbents formed from hydrolyzed cross-linked polyacrylamides, polyacrylates, polymers of acrylic polymers, or their copolymers. Such materials when lightly cross-linked are insoluble and when dry are solids that may be blown in an air stream. A preferred material is a sodium polyacrylate hydrocolloidal particle such available from Grain Processing Corporation as Waterlock J-500. The superabsorbent particle may be of any desired shape such as fibrous or round, flakes or irregular.

The staple fiber blown into the coform may be any fiber that improves the absorbency or other property of the coform. Suitable fibers include polyester fibers, nylon fibers, and cotton fibers. The preferred fiber is a wood fiber as the wood fibers formed from pulp are of desired size, low in cost, and of high absorbency.

In the structure of the invention superabsorbent may be added in any amount from a very minimum to an upper range which would be the amount that would stay in the composite without causing the composite to lose its integrity or the superabsorbent to be easily shaken loose. A suitable amount of superabsorbent generally is between about 2.0 and about 60 percent by weight of the layer containing the superabsorbent. A preferred amount of superabsorbent is between about 5 percent and about 22 pecent by weight of the layer containing superabsorbent for high absorbence and good fabric strength. The preferred superabsorbent containing coform layers has between about 11 and about 55 grams of superabsorbent per square meter for a substrate that without superabsorbent would weigh about 100 grams/sq.meter. Generally the coform portion is preferred to be in a range of about 70 percent pulp and about 30 percent polymer for high absorbency and good handling properties.

The invention has been described with the formation of coform material. It is also within the invention to form successive layers of air-formed meltblown sheet material, not containing additional staple fibers, in which the first layer is without superabsorbent while the second or other successive layer does contain superabsorbent. The phrases "meltblown layer" and "meltblown sheet" as used herein mean an air-formed meltblown polymer fiber layer of entangled fibers not containing staple fibers whereas the term "coform" is a layer, as previously described, that contains staple fibers in addition to meltblown fibers. The formation of air-formed entangled meltblown fiber sheet materials with superabsorbents is described in U.S. Pat. No. 4,429,001—Kolpin et al. and British Patent Application Publication No. 2,113,731 of Aug. 10, 1983, both herein incorporated by reference.

The formation of layered meltblown absorbent structures in which the exposed body-side liner does not contain superabsorbent also would have the advantages as in the coform structures of not exposing a slimy surface and also being less likely to lose superabsorbent particles during handling. A layered meltblown structure could be formed by the illustrated apparatus of the drawings of FIGS. 1, 2, and 5 by not operating the wood pulp divellicating apparatus. In another alternative embodiment, a structure of one or more coform layers in integral combination with one or more meltblown layers is also possible. Any or all layers except the body-side or exposed layer could have superabsorbent. Coform structures are preferred over meltblown fiber layers for most purposes as they are higher in absorbency.

A surface layer of only meltblown fibers with interior layers of coform would have increased abrasion resistance and strength. A meltblown interior layer containing superabsorbent and surface layer or layers of coform would have better holding of the superabsorbent powder in the article. The formation of various combinations of meltblown and coform layers is within the invention as is the placement of superabsorbent in either the meltblown or coform layer.

The superabsorbent containing product of the invention finds uses in a variety of fields. It is particularly suitable for use in products such as perineal shields and undergarments for the incontinent. It has a very high absorbency as well as the ability to retain fluids. It also has a high ability to transmit fluids from the point of application to other portions of the garment where the fluid may be absorbed rather than leaking from the garment. It also is suitable for bedpads, diapers, feminine care products, and for body dressings such as those for wounds. It is particularly desirable where high liquid absorbency is desired at relatively low cost with good retention of superabsorbent during handling and no exposure of superabsorbent to the skin. The product also exhibits good retention of liquids in the composite sheet when the sheet is compressed or manipulated.

EXAMPLE

A composite fabric in accordance with the invention is prepared in accordance with the general procedure described above and illustrated in FIG. 1. Polypropylene resin (PD 701—Hercules) is extruded from a series of orifices numbering approximately 1200 across a 60-inch width. The extrusion rate is at about 5 pounds per inch per hour from each of the 2 banks. The extrusion is at a final temperature of about 600° F. and fibers are attenuated in primary air streams flowing at a sonic velocity and a combined rate of about 900 SCFM at a temperature of about 600° F. The secondary air stream containing suspended pulp fluff is comprised of Southern pine bleached kraft with softening agents. The pulp is picked and forced into a fiber jet approximately 1½–2 inches from the primary air stream and 1½–2 inches below the die tip. The gas flow to the picker unit is about 2000 SCFM, and stream is directed perpendicular to the flow of the primary air. The velocity of the primary air is between about 5 and 10 times the velocity of the secondary stream at the point it is introduced. Superabsorbent particulates (Grain Processing Corporation Waterlock J-500 sodium polyacrylate superabsorbent) having a particle size of about 150–200 microns are introduced at a point slightly above the pulp nozzle from a tertiary air stream whose velocity is estimated to be between 1/5 and 1/10 the velocity of the primary air stream. The composite web is collected on a wire mesh belt, the belt is about 16 inches below the extrusion die tip. The meltblown unit in which superabsorbent is added is placed about 17 feet downstream from the first meltblown stream system and is identical to the first meltblown system except for not having the apparatus for addition of superabsorbent. The composite layer not containing superabsorbent comprises by weight about 70 percent cellulose fibers and about 30 percent meltblown polypropylene microfibers. The layer containing superabsorbent comprises by weight about 25 percent superabsorbent, 52 percent cellulose fiber, and 23 percent polypropylene microfibers. The formation of the second layer that contains superabsorbent results in a second layer of substantially the same thickness as the first layer that does not contain superabsorbent. Therefore, the superabsorbent material is located generally within the fiber interstices and does not significantly affect the bulk of the product. The composite product has the following measurements:

Basic Weight: 232 g/m2
Uncompressed Thickness: 0.200 inches

The web has a felt-like or cloth-like feel, was compressible and cushiony, and conformable and nonpapery. Further, when wet the product exhibits a nonclammy feel on the coform side while the side containing superabsorbent exhibits the clammy, slimy feel of superabsorbent-containing materials. Further, it is found that substantially all the superabsorbent applied to the process was entrapped in the product as the dust collector does not exhibit significant collection of superabsorbent during layer formation.

I claim:

1. An absorbent dressing comprising an impervious polymer backing sheet, a pervious body-side liner, and an absorbent core located between said pervious liner and said impervious backing wherein said absorbent material comprises a layered nonwoven fabric-like material having a unique combination of strength, absorbency and hand, said material comprising:

A. at least one normal absorbent layer of a gas-formed matrix of thermoplastic polymeric meltblown microfibers and a multiplicity of individualized and gas-formed staple fibers disposed throughout said matrix of microfibers and engaging at least some of said microfibers from each other to space the microfibers apart from each other, said staple fibers being interconnected by and held captive within said matrix of microfibers by mechanical entanglement of said microfibers with said staple fibers, the mechanical entanglement and interconnection of said microfibers and staple fibers forming a coherent integrated fibrous structure, and B. at least one highly-absorbent layer integrally connected to said normal absorbent and highly-absorbent layer comprising a gas-formed matrix of thermoplastic polymeric meltblown microfibers and a multiplicity of individualized and gas-formed staple fibers and superabsorbent particles disposed throughout said matrix of microfibers and engaging at least some of said microfibers to space the microfibers apart from each other, said staple fibers and said superabsorbent being interconnected by and held captive within said matrix of microfibers by mechanical entanglement of said microfibers with said staple fibers and said superabsorbent particles, the mechanical entanglement and interconnection of said microfibers and staple fibers and said superabsorbent particles forming a coherent integrated fibrous structure.

2. The absorbent dressing of claim 1 wherein a normal absorbent layer is located adjacent said pervious liner.

3. The dressing of claim 2 wherein said at least one normal absorbent layer and said at least one highly absorbent layer are integrally connected by intermingling of fibers.

4. The dressing of claim 1 wherein said absorbent material comprises a normal absorbent layer on each surface and an interior layer comprising at least one highly absorbent layer.

* * * * *